US007278414B2

(12) United States Patent
Diem

(10) Patent No.: US 7,278,414 B2

(45) Date of Patent: Oct. 9, 2007

(54) DIAGNOSTIC TOOL FOR SENSING OXYGEN SENSOR HEATER OPERATION

(75) Inventor: Earl D. Diem, Ortonville, MI (US)

(73) Assignee: Delphi Technologies, Inc., Troy, MI (US)

(*) Notice: Subject to any disclaimer, the term of this patent is extended or adjusted under 35 U.S.C. 154(b) by 37 days.

(21) Appl. No.: 11/118,199

(22) Filed: Apr. 29, 2005

(65) Prior Publication Data

US 2006/0247842 A1 Nov. 2, 2006

(51) Int. Cl.
*F02D 41/00* (2006.01)
*G01N 33/497* (2006.01)

(52) U.S. Cl. ...................................... 123/688; 73/23.32

(58) Field of Classification Search ................ 123/688, 123/697; 73/23.32, 116, 117.3, 118.1
See application file for complete search history.

(56) References Cited

U.S. PATENT DOCUMENTS 5,669,219 A * 9/1997 Schnaibel et al. ............ 60/274
5,709,198 A * 1/1998 Sagisaka et al. ............ 123/684
5,974,857 A * 11/1999 Yamashita et al. ......... 73/23.32
6,009,866 A * 1/2000 Sagisaka et al. ............ 123/681
6,314,790 B1 * 11/2001 Sagisaka et al. ........... 73/23.31
6,543,220 B2 * 4/2003 Yoshida et al. ............... 60/285
6,604,007 B2 * 8/2003 Leven et al. .................. 700/79
6,947,817 B2 * 9/2005 Diem .......................... 701/34
2002/0026822 A1 * 3/2002 Reading et al. ............ 73/31.05

* cited by examiner

*Primary Examiner*—John T. Kwon
(74) *Attorney, Agent, or Firm*—Jimmy L. Funke

(57) ABSTRACT

A diagnostic testing system for a vehicle comprising an oxygen sensor having a heating element for heating the oxygen sensor to its minimum operational temperature, an analyzer having a user interface, a communications link between the analyzer and the vehicle to obtain data from the oxygen sensor, and a diagnostic heuristic analyzing the data and confirming proper operation of the heating element, the diagnostic heuristic being adapted to generate an output and transmit the output to the user interface, the output including the results generated by analysis of the data by the diagnostic heuristic.

13 Claims, 5 Drawing Sheets

DIAGNOSTIC TOOL FOR SENSING OXYGEN SENSOR HEATER OPERATION

FIELD OF THE INVENTION

The present invention relates generally to oxygen sensors and, more particularly, to a system and method for automating and standardizing the diagnostic testing for verifying the operation of a heating element component of oxygen sensors.

BACKGROUND OF THE INVENTION

An oxygen sensor is used for monitoring the amount of oxygen present in the air/fuel mixture of an internal combustion engine. Oxygen sensors are part of the emissions control system of a vehicle and are typically assembled to an exhaust pipe downstream from the combustion process so that a nose of the oxygen sensor protrudes into the exhaust pipe so that it may sample the combustion gases produced by the engine. The data obtained by the oxygen sensor helps to determine the combustion efficiency of the engine air/fuel mixture. Typically, the stoichiometric air/fuel ratio theoretically necessary for complete combustion is 14.7 to one (14.7 kg of air to 1 kg of fuel). A powertrain control module (PCM) uses data obtained from the oxygen sensor to adjust the amount of air and fuel entering the engine to maintain the desired air/fuel ratio.

A complete combustion process is ideal for a number of reasons. If the combustion process involves a lower level of air (i.e., a higher level of fuel), a "rich" condition exists and not all of the raw fuel will be completely burned in the combustion chamber leading to an increase in hydrocarbon (HC) and carbon monoxide (CO) emissions from the vehicle. If the combustion process involves a higher level of air (i.e., a lower level of fuel) a "lean" condition exists and the combustions temperatures will elevate, leading to increased levels of nitrogen oxides (NOx) being emitted from the vehicle as well as a the potential to damage the engine and/or catalytic converter.

Generally, oxygen sensors must be heated to temperature prior to beginning the monitoring process. In one embodiment of a known oxygen sensor, the operational temperature of the oxygen sensor is 574 degrees Fahrenheit (° F.). Using this known sensor, while the oxygen sensor is heating to its operational temperature, the engine runs in a so-called "open loop" condition. In practice, the heating takes place using the heat of the combustion gases. As a result, during the heating process, involving actual engine combustion, the PCM does not receive any data from the oxygen sensor on the quality of the combustion gases. While the PCM may adjust the air and fuel based on its best estimates from environmental conditions, the PCM may not be able to obtain the most desired stoichiometric air/fuel ratio to optimize combustion. After the prior art oxygen sensor is brought up to temperature, the engine runs in a so-called "closed loop" condition. When in a closed-loop condition the PCM may obtain data from the oxygen sensor about the quality of the combustion gases and adjust the air/fuel mixture, accordingly.

Heating elements have been developed and added to oxygen sensors in an attempt to heat the oxygen sensor to its operational temperature without having to rely solely on the gases of combustion. The heating element is typically activated as the ignition is turned to the ON position. In practice, these types of oxygen sensors can usually be brought up to operational temperature in less time than sensors that do not have such a supplemental heating mechanism so that the PCM and engine can enter the "closed loop" condition more quickly, permitting the earlier adjustment after engine startup of the air and fuel mixture. Overall pollution related emissions are decreased. Fuel economy is improved. Moreover, powertrain durability is enhanced.

With the ever increasing requirement for vehicle-based on-board diagnostics (OBD), millions of vehicles are brought to dealerships or service stations across the world for problem diagnosis and repair. In the field of vehicle service, verifying the heater operation of an oxygen sensor is not standardized. Also, many service technicians do not fully understand the operation of oxygen sensors. Unfortunately, lack of understanding often leads to fully operational oxygen sensors being inadvertently replaced on vehicles because there is no standard for service technicians to follow. The disclosed diagnostic tool provides an innovative approach to standardizing and automating the verification of heater operation of a vehicle-based oxygen sensor used in conjunction with regulating the air/fuel ratio of combustion gases.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION

The present invention is directed towards a system and method to nonintrusively conduct diagnostic testing to determine the performance of a heating element of an oxygen sensor positioned in the exhaust system of an internal combustion engine. The engine is typically not running while the test is undertaken; however, the ignition is in the "ON" position. This test procedure is commonly known as "Key On, Engine Off" (KOEO) testing. The system and method guides a technician through various inspection processes that result in diagnostic testing of the heating element. During any particular inspection process, the system collects and records data received from the oxygen sensor through an on-board vehicle control module. Once a particular step in the inspection method is complete, the system will analyze the collected data to determine the next step in the inspection process. Oxygen sensors are a source of diagnostic information and often an overlooked service component.

I. System Overview

Figure 1:
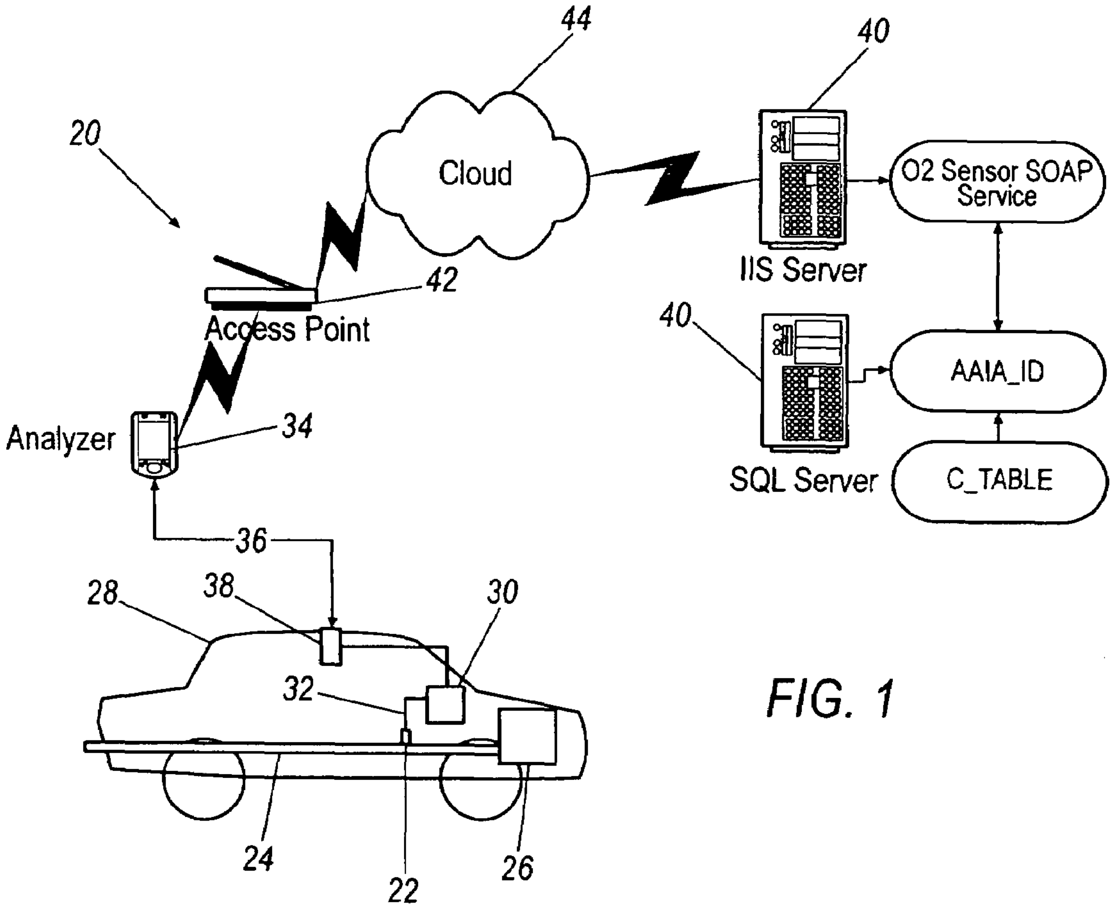
FIG. 1 is an environmental view of an oxygen sensor diagnostic system.

FIG. 1 is an environmental view of a diagnostic system 20 according to a disclosed embodiment. An oxygen sensor 22 is located in the exhaust stream 24 of an internal combustion engine 26 associated with a vehicle 28. Oxygen sensor 22 is part of an emissions control system and is in communication and typically sends data to an on-board vehicle control module 30 such as a powertrain control module (PCM) or engine control module (ECM). While the discussion below focuses on the PCM, any appropriate or combination of modules may be used.

The purpose of oxygen sensor 22 is to provide PCM 30 with data that may be used to calculate the efficiency of the engine combustion process. PCM 30 uses this information to adjust the intake of outside air into engine 26 and/or to adjust the amount of fuel being delivered to engine 26 during "closed loop" engine operations. By utilizing data from oxygen sensor 22, PCM 30 can make adjustments to fuel and air delivery to engine 26 that results in a more complete combustion within engine 26, thereby lowering emissions and increasing fuel economy.

For the purposes of testing the operation of oxygen sensor 22, it is possible to connect an analyzer 34 such as a hand held computer to vehicle 28 by way of an interface cable 36. Analyzer 34 typically includes an input mechanism such as a microphone, mouse, keyboard, or touch screen, and an output mechanism such as a screen or sound system. Analyzer 34 utilizes a software system to facilitate a data interface between analyzer 34 and vehicle 28, data communications from vehicle 28, and even diagnostic analysis in the form of a diagnostic heuristic including software used to analyze the data and confirm proper operation of the sensor in the manner discussed below.

In one preferred embodiment, analyzer 34 is connected using a communication link such as a serial data bus 38 associated with a vehicle bus interface, that in turn is connected preferably in real time to appropriate various vehicle systems such as PCM 30 and ultimately oxygen sensor 22. In some embodiments, data may be read directly from PCM 30. Thus, oxygen sensor 22 may be tested without disturbing any sensor connectors or wiring associated with oxygen sensor 22. As a result it is possible to confirm that not only is oxygen sensor 22 operational, but so is the entire interface between oxygen sensor 22 and related vehicle components such as PCM 30.

In turn, analyzer 34 is in selective communication with one or more servers 40. Server 40 typically contributes to the operation of the diagnostic heuristic as discussed below. In the illustrated embodiment, analyzer 34 has a wireless interface with an access point 42, and then by means of a data transmission cloud 44, which may be a mixture of wired and wireless communication protocols, the information is exchanged with server 40. Of course, other approaches may be used including the storing of data on analyzer 34 until it is is docked with a fixed unit used to transmit data; a data mechanism such as a data card or floppy associated with analyzer 34 may be used to complete data transmission between analyzer 34 and server 40; or the complete diagnostic analysis may take place within analyzer 34 itself using a diagnostic heuristic as part of the software system.

Oxygen sensors are not fully operational until heated to a specified minimum operational temperature. For a known zirconia oxygen sensor, the minimum operational temperature is approximately 574 degrees Fahrenheit (° F.). After the oxygen sensor 22 is heated to a minimum operational temperature it will compare the ambient oxygen (AO2) level to the amount of oxygen exiting engine 26 through the exhaust (EXO2) stream 24 post combustion. A difference in the level of AO2 as compared to EXO2 will cause an analog voltage to be produced by the oxygen sensor. The greater the difference between EXO2 and AO2, the higher the voltage produced. For one known zirconia oxygen sensor, the voltage can range between 0 V up to 1.5 V in Death Valley, Calif., 1.1 V at Sea Level, and 0.9 V in Denver Colo. For another known zirconia oxygen sensor, the voltage can range between 0 V up to 1.125 V.

Figure 2:
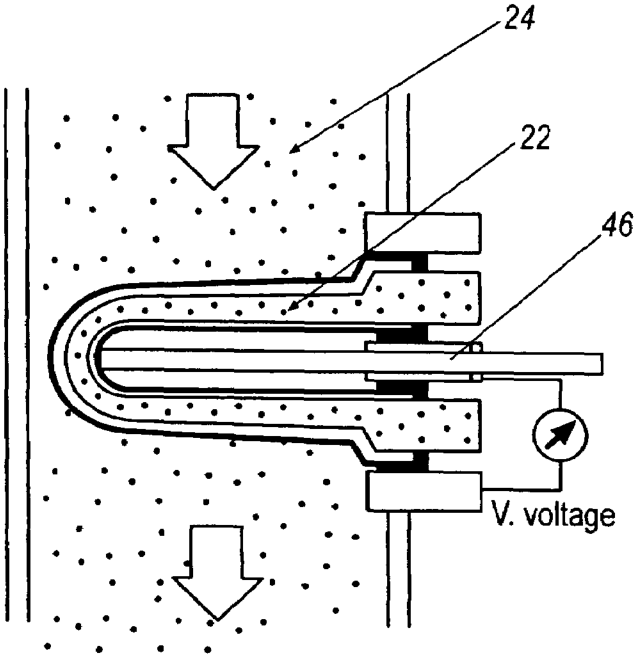
FIG. 2 is a cross-sectional view of an oxygen sensor according to an embodiment of the present invention.

Now referring to FIG. 2, there is illustrated a cross-sectional view of a typical oxygen sensor 22 with a separate heating element 46. A conventional non-heated oxygen sensor relies solely on the exhaust gases to heat the sensor, whereas oxygen sensor 22 has the advantage of also using the heating element 46 to heat oxygen sensor 22 to a minimum operational temperature. Oxygen sensor 22 and a non-heated oxygen sensor are distinguished by the amount of time required to heat the sensor to its minimum operational temperature. The difference between the two sensors is manifested in the approaches taken to heat the sensors to a minimum operating temperature. As will be appreciated, oxygen sensor 22 with heating element 46 may be heated to a minimum operational temperature more quickly than a conventional non-heated oxygen sensor. This time difference allows for PCM 30 to enter "closed loop" operation in less time. As a result, powertrain durability may be improved, pollution based emissions reduced, and fuel economy enhanced.

PCM 30 is calibrated in such a manner that a bias voltage is established in oxygen sensor 22, which represents the median between a "large" O2 content (0-449 mV) known as a "lean" combustion mixture of fuel and air and a "small" O2 content (451 mV+) known as a "rich" combustion mixture of fuel and air. Typically, the stoichiometric combination of fuel and air for a theoretical complete combustion is 14.7 to one (14.7 kg of oxygen to 1 kg of fuel). Using the exemplary ratio, a lean combustion mixture would be a stoichiometric combination greater than 14.7 to one and a rich combustion mixture would be a stoichiometric combination less than 14.7 to one. In the illustrated embodiment, 450 mV represents a calibrated median bias voltage where AO2 is approximately equal to EXO2.

To protect the integrity of emissions components such as the catalytic converter associated with exhaust systems of automotive vehicles sold in many countries and to provide the operator with the greatest amount of performance, PCM 30 constantly adjusts fuel delivery to the cylinders via short term fuel trim calculations and by controlling both injector pulse width and ignition dwell time so that the average high and low value is the median voltage level (e.g., 450 mV) at idle or steady cruise operations.

Figure 3:
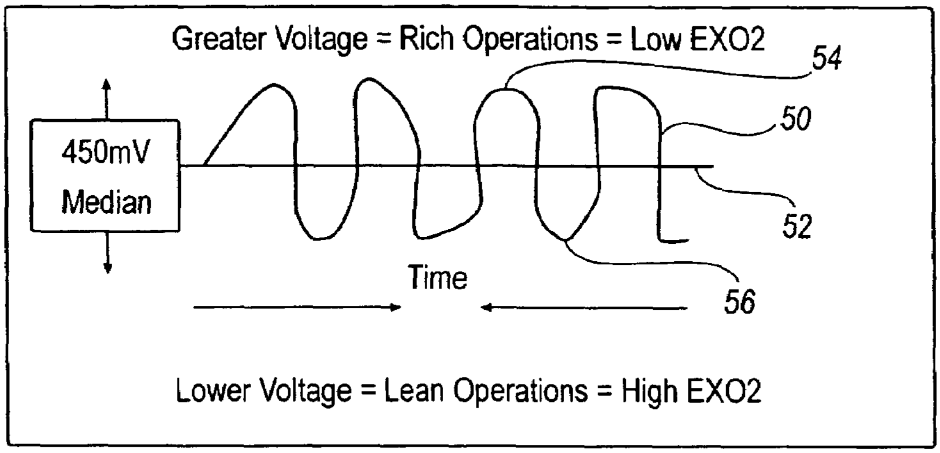
FIG. 3 is a graph showing an oxygen sensor voltage versus time as measured between an upper voltage limit and a lower voltage limit.

As such, as illustrated in FIG. 3, a typical calibrated oxygen sensor viewed using an oscilloscope or with a graphing scan will generate a fluctuating voltage line 50 with a generally continuous sinusoidal representation passing through the median voltage level 52 (e.g., 450 mV) between an upper voltage 54 (e.g., 800 mV) and a lower voltage 56 (e.g., 175 mV). FIG. 3 illustrates that a rich mixture with a lower amount of oxygen in the exhaust stream results in higher voltages than does a lean mixture with a higher amount of oxygen in the exhaust stream.

Thus, under expected operating conditions, oxygen sensor 22 should display the following three basic performance criteria if it is operating properly: (1) oxygen sensor 22 should have a voltage level at an upper range of 800 mV or more when driven rich; (2) oxygen sensor 22 should have a voltage level at a lower range of 175 mV or less when driven lean; and (3) the voltage response time from lean to rich and vice versa as shown by the generally sinusoidal representation should be less than 100 milliseconds (ms).

As discussed in greater detail below, PCM 30 expects the generated voltage from oxygen sensor 22 to pass through the median within a predetermined period of time. PCM 30 uses this information to determine the effectiveness and quality of oxygen sensor 22. If there is no response from oxygen sensor 22 (open) or a constant singular response from oxygen sensor 22 (shorted to ground or power), a diagnostic trouble code (DTC) will be set by PCM 30. Also, if oxygen sensor 22 fails to respond to a rich command or a lean command within a given amount of time, a sensor performance DTC will be stored in the memory of PCM 30.

II. Test Procedure

A. Oxygen Sensor Temperature Status

Figure 4:
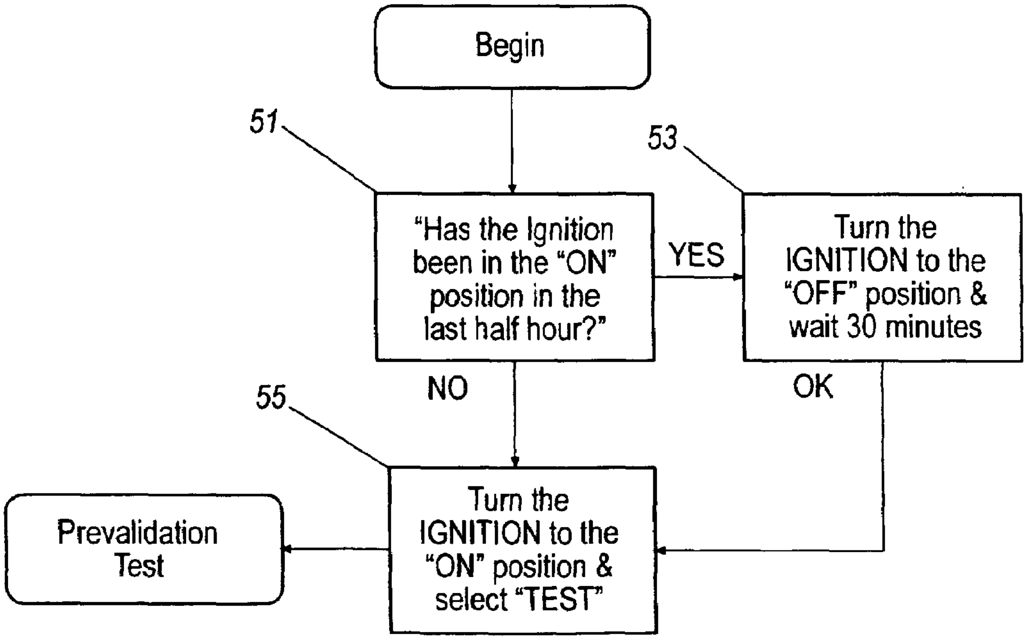
FIG. 4 is a flow chart showing a cool down preparation sequence.

Before the heater operation of oxygen sensor 22 may be tested, the exhaust system and oxygen sensor 22 must be conditioned by going through a cool down period of at least one-half hour. This is to assure that the temperature of oxygen sensor 22 will be below its minimum operational temperature of 574 degrees ° F. As a result, oxygen sensor 22 will execute a warm up cycle for analysis when the test is performed. FIG. 4 illustrates the steps taken to verify that oxygen sensor 22 has been properly cooled below its minimum operating temperature prior to beginning the test. The technician will be instructed to allow the vehicle to go through a one-half hour cool down period prior to beginning any testing of the heater operation of oxygen sensor 22. The technician will be asked whether the ignition has been in the ON position in the last one half hour as shown at point 51. If the ignition has been in the ON position at any time during the last half hour, the technician will be instructed to ensure the ignition is presently in the off position and to wait one half hour prior to beginning the test as shown at point 53. If the ignition has been in the ON position within the last half hour prior to testing of the heater operation of oxygen sensor, incorrect test results may be obtained. When the technician has waited the one-half hour, the technician will be instructed to turn the ignition to the ON position and press TEST on analyzer 34 to being the testing procedure as shown at point 55.

B. Establish Communications

Figure 5:
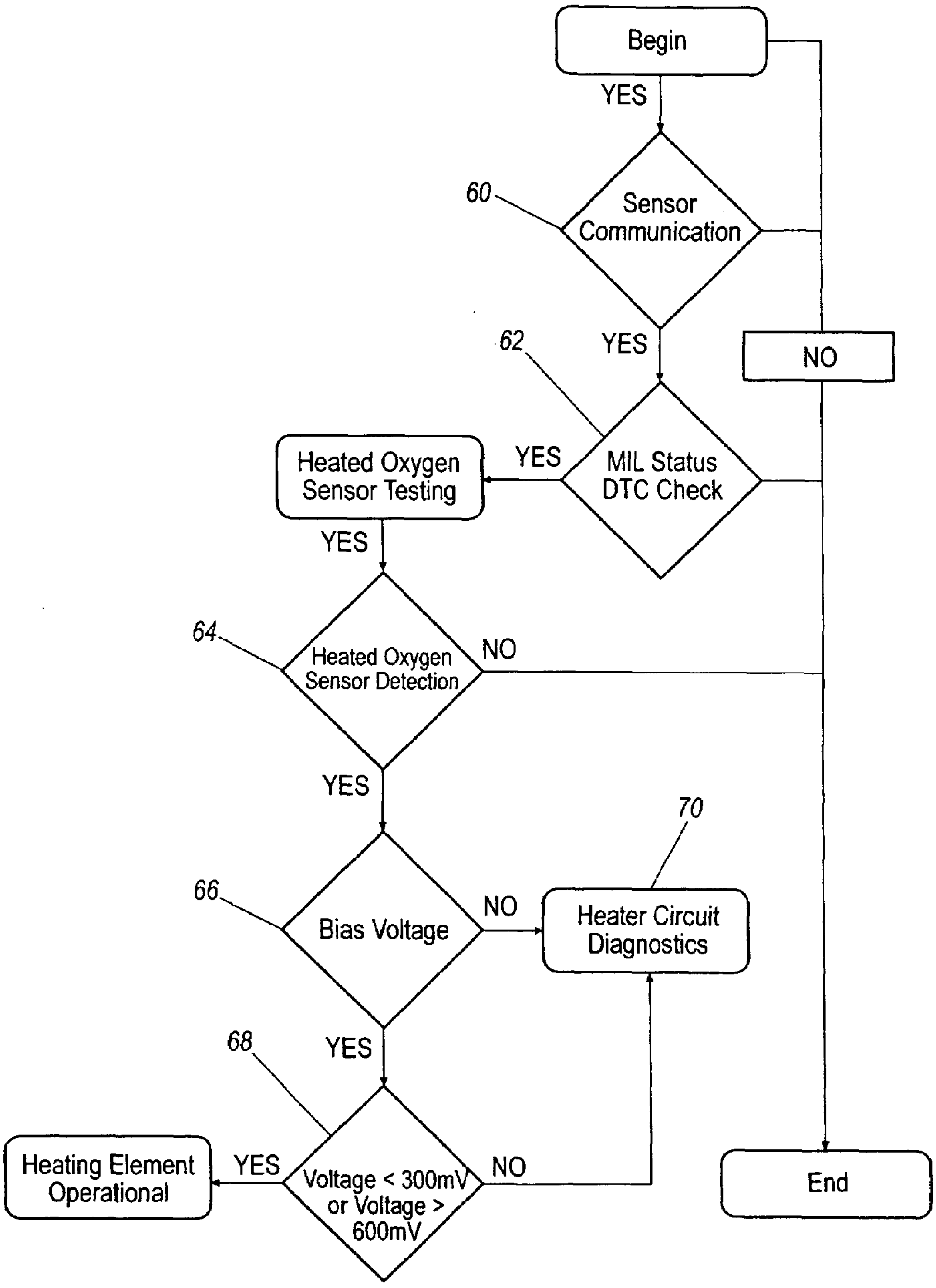
FIG. 5 is a flow chart showing oxygen sensor pre-validation system checks and oxygen sensor testing.

Oxygen sensor 22 pre-validation system checks are shown in FIG. 5. Prior to conducting diagnostic testing of oxygen sensor 22, communications with PCM 30 may be established at decision point 60 in a manner known to those of ordinary skill in the art, such as according to Delphi's Integrated Service Solutions (ISS) guidelines, which are hereby incorporated herein in their entirety. However, establishing communication between system 20 and PCM 30 is not limited to the guidelines under Delphi's ISS, and may be established under any system that includes a hardware reset and automatic vehicle communication protocol detection. The establishing of communication will include a hardware reset and automatic vehicle communications protocol detection. This procedure is preferably in compliance with the procedures set forth in SAE document J1979 for automatic protocol detection, which is hereby incorporated herein in its entirety.

C. Pre-Test Validation and Test Conditioning

Initially, pre-validation testing is performed to determine the status of various systems within vehicle 28. Insuring specific conditions have been achieved prior to conducting diagnostic testing of oxygen sensor 22 prevents the technician from conducting inaccurate diagnostic testing. Moreover, the likelihood of a working oxygen sensor 22 being replaced based upon an incomplete or incorrect, diagnostic testing of oxygen sensor 22 is reduced.

Preferably, analyzer 34 presents a user-interface much like that shown in FIG. 5. If any of the pre-conditions are not satisfied, then pre-validation terminates with an error message. If the tests are satisfied, then system 20 moves onto oxygen sensor system testing.

MIL Status and DTC Check

An on-board control module such as the on-board diagnostic (OBD) II system is polled at point decision 62 for malfunction indicator light (MIL) status and stored diagnostic trouble codes (DTCs) as part of the pre-test conditioning checks. If the MIL is commanded ON, or a DTC is stored other than a code that is designated as an oxygen sensor code, the test will be aborted and the user advised of the trouble code(s). Therefore, if a stored DTC is encountered during PCM 30 inspection sequence that may affect testing of oxygen sensor 22, the fault code will be communicated to the technician through analyzer 34 and diagnostic testing of oxygen sensor 22 will be aborted.

The test will instruct the user to repair the reason for the MIL ON or non-oxygen sensor DTC and instruct the user to retest after the repair. In addition to the examples given above, another example of a potential DTC is a bad connection between a particular sensor and PCM 30.

The providing of DTCs through analyzer 34 permits the technician to fix known problems. Lists of DTCs are available for most carmakers and are known in the art. Once the fault code has been corrected, the technician may repeat the initial pre-validation testing for stored fault codes.

In the alternative, if there are not codes that have to be considered then the system moves onto heated oxygen sensor testing.

C. Oxygen Sensor Detection

Once the technician has started the testing, the test will automatically determine the configuration of oxygen sensor 22. In a preferred embodiment this is first accomplished by first issuing a Mode 01 PID 13 at decision point 64 to determine:

1) The support of PID 13;
2) If B1S1 is present; and
3) If B2S2 is present.

If a negative response to PID 13 is received, PID 1D will be sent to determine:

1) The support of PID 13;
2) If B1S1 is present; and
3) If B2S2 is present.

If a negative response to PID 1D is received, PID 24 will be sent to determine if the vehicle is equipped with AFR or Wide Range Fuel Sensors. If a positive response to PID 24 is received, then the technician will be informed that the vehicle is equipped with Wide Range Fuel Sensors, which are not supported at this time and the test will be aborted. If the sensor cannot be detected at all, the test will also be aborted.

D. Heater Event Recording

Once the oxygen sensor configuration has been established, the test will record the activity of oxygen sensor 22 that is present on vehicle 28 for one and one-half minutes. This is meant to capture the oxygen sensor warm up cycle by recording the oxygen sensor voltage while it is heated and becomes active (i.e. the oxygen sensor is heated to its operational temperature). Analyzer 34 records the data for analysis.

E. Data Analysis

Oxygen sensor 22 with an operational heating element 46 will exhibit a sensor voltage at or near the 450 mV bias voltage and gradually decrease to below 100 mV in less than one and one-half minutes if the exhaust is full of fresh air. Alternatively, however, if the exhaust is full of unburned fuel, the oxygen sensor voltage will increase to some point above 600 mV and remain there during the warm up cycle. The point of the test is not the direction the voltage goes during the warm-up cycle, but rather, oxygen sensor 22 is heated to its operational temperature and becomes active as indicated by the movement toward either rich or lean voltage output.

The test uses a data analysis algorithm that performs the following functions:

1. The bias voltage status of oxygen sensor 22 is determined as shown at decision point 66. The first five frames of oxygen sensor 22 data will be analyzed to meet a bias voltage window of between 400 mV to 500 mV. An average of the first frames will be calculated and saved for the diagnostic test result. If the bias voltage cannot be appropriately determined, then the system goes to point 70, entitled Heater Circuit Diagnostics, as discussed below.

2. Once the bias voltage has been established for the oxygen sensor being tested, the algorithm as shown at decision point 68 will monitor the oxygen sensor data status and stop recording if the data meets one of the following criteria:

a. The oxygen sensor voltage reaches a state of less than 300 mV; or b. The oxygen sensor voltage reaches a state of greater than 600 mV.

3. The algorithm will record 20 frames of data past the point of reaching either threshold voltage in function number 2 above.

F. Test Results

Oxygen sensor 22 will pass the test if, first, the bias voltage threshold of 450 mV is achieved within the first five frames of recorded data. This data informs the technician whether heating element 46 is operational. And, second, if the voltage of oxygen sensor 22 crosses the activity threshold of above 600 mV (raw fuel in the exhaust) or below 150 mV (fresh air in the exhaust) during the one and one-half (1.5) minute recording.

Oxygen sensor 22 will fail the test if the bias voltage threshold of 450 mV is not achieved within the first 5 frames of data, or the voltage of oxygen sensor 22 does not cross the activity threshold of above 600 mV or below 300 mV during the one and one-half (1.5) minute recording. The voltage of a oxygen sensor that remains between 300 mV and 600 mV is deemed inoperative.

III. Heater Circuit Diagnostic

Figure 6:
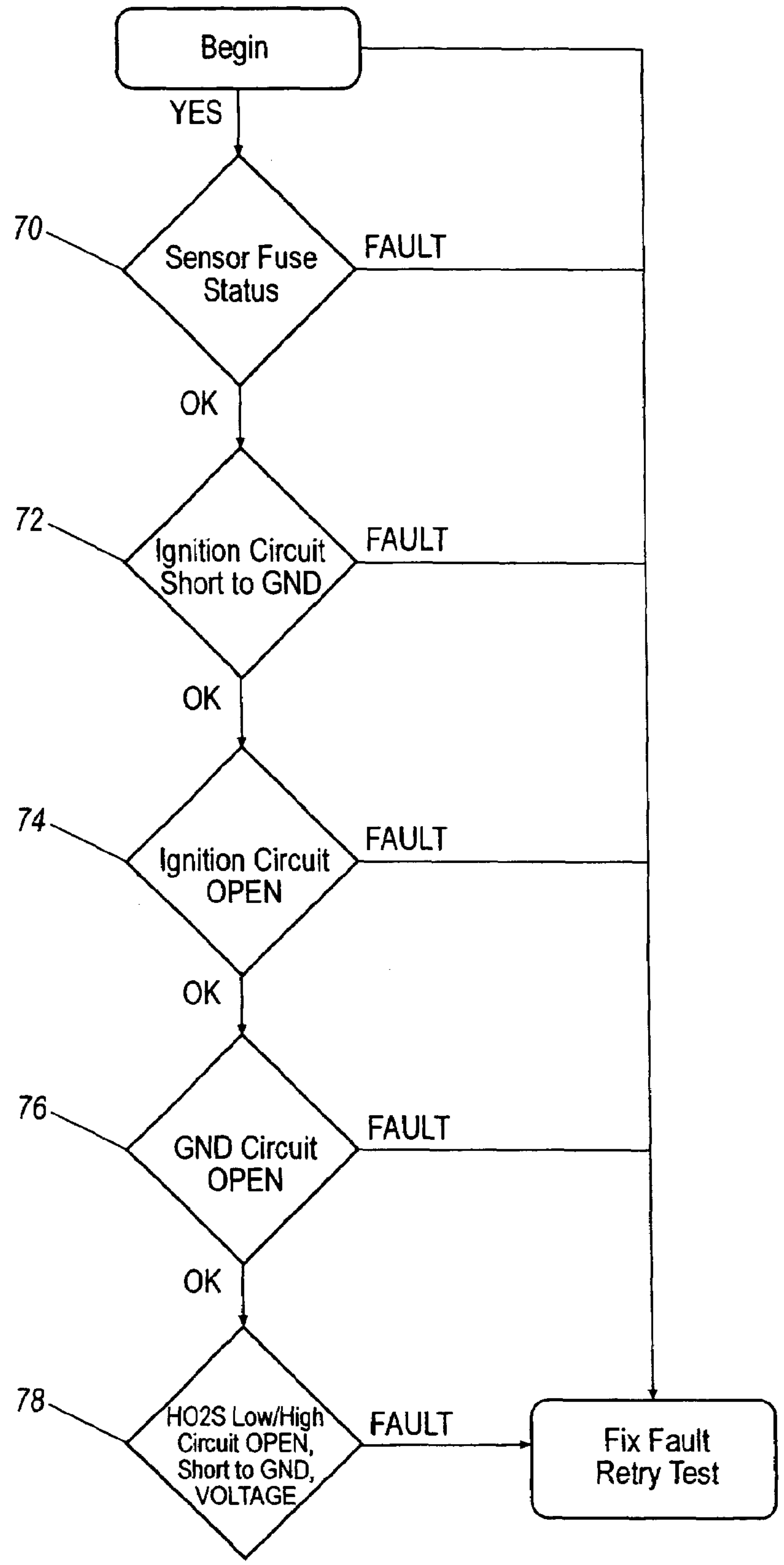
FIG. 6 is a flow chart showing heater circuit diagnostics.
Figure 7:
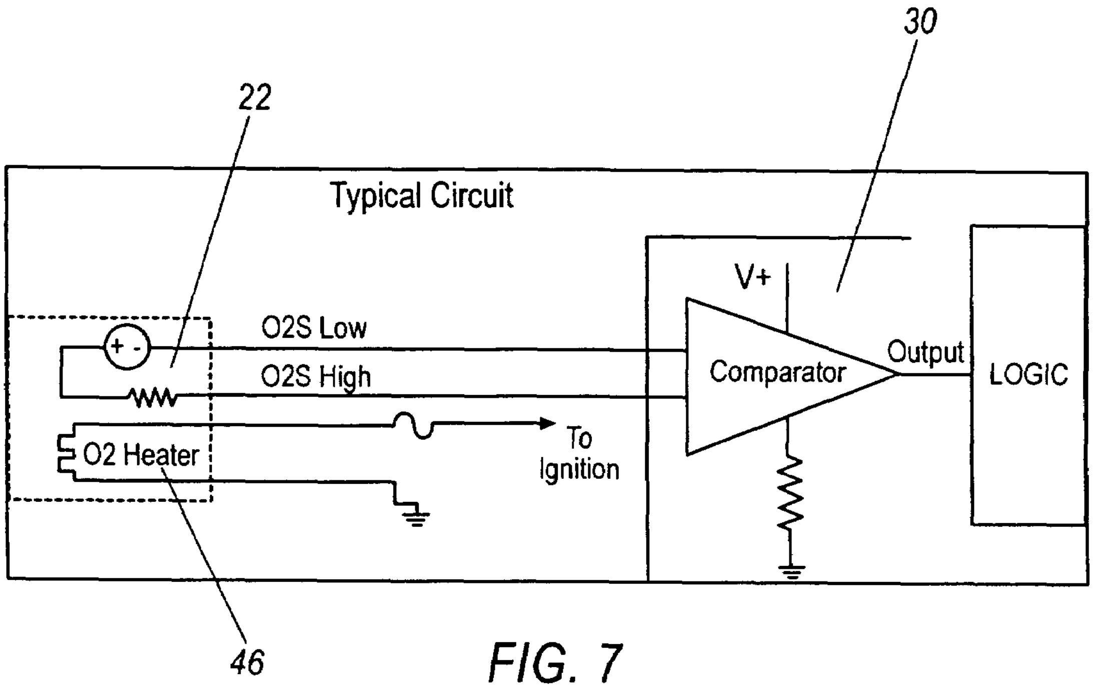
FIG. 7 is a schematic representation of the oxygen sensor according to an embodiment of the present invention.

If oxygen sensor 22 fails, the technician will be given an opportunity to enter a "Heater Circuit Diagnostic" mode at point 70, as illustrated in more detail in FIG. 6, for oxygen sensor 22 in an attempt to isolate the cause of failure. The Heater Circuit Diagnostic mode will analyze the circuit illustrated in FIG. 7 and guide the user to validation of the following as represented by the indicated decision points:

1. Oxygen sensor fuse status as shown at point 70;

2. Ignition circuit short to ground as shown at point 72;

3. Ignition circuit open/change in resistance as shown at point 74;

4. Ground circuit open/change in resistance as shown at point 76; and

5. Oxygen sensor low/high circuit for open, short to ground, short to voltage, or change in resistance as shown at point 78.

The diagnostic will log the fault to the report when the circuit failure is identified.

IV. Printing and Storing Test Results

After the testing has been completed, a summary report of the test event will be displayed. This page will be printable to a report format to the local or network printer as available. All graphs presented during the test must be printable.

Results of the test will be stored as a diagnostic result in the following manners:

1. In a non-iSHOP system, the results will be stored to the Current RO, in the facility table on the web SQL server and be available from RO history; or 2. In an iSHOP environment, the result will be stored to the iSHOP server hosted by the SMS on the Local LAN.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A diagnostic testing system for a vehicle comprising:

an oxygen sensor having a heating element for heating the oxygen sensor to its minimum operational temperature;

an analyzer having a user interface;

a communications link between the analyzer and a vehicle to obtain data from the oxygen sensor; and a diagnostic heuristic for analyzing the data and confirming proper operation of the heating element;

the diagnostic heuristic being adapted to generate an output and transmit the output to the user interface, the output including the results generated by analysis of the data by the diagnostic heuristic.

2. The diagnostic testing system of claim 1 wherein the oxygen sensor is held below its minimum operational temperature for a predetermined period of time prior to commencing operation of the diagnostic heuristic.

3. The diagnostic testing system of claim 1 wherein the data from the oxygen sensor, when heated to its minimum operational temperature, includes a voltage.

4. The diagnostic testing system of claim 3 wherein the voltage varies between an upper voltage limit and a lower voltage limit in a generally sinusoidal manner over time, the diagnostic heuristic being configured to combine the voltage with elapsed time to analyze operation of the heating element.

5. A diagnostic testing system of claim 4 wherein the diagnostic heuristic is configured to measure a time period between one of the upper and lower voltages and the other of the upper and lower voltages in analyzing operation of the heating element.

6. The diagnostic testing system of claim 1 wherein the diagnostic heuristic includes a set of instructions presented through the user interface.

7. The diagnostic testing system of claim 3 wherein the diagnostic heuristic is configured to collect the data over a predetermined period of time for use by the diagnostic heuristic to analyze operation of the heating element.

8. The diagnostic testing system of claim 3 wherein the oxygen sensor, when heated to its operational temperature, includes a bias voltage.

9. A diagnostic testing system for a vehicle having an internal combustion engine comprising:

an oxygen sensor having a heating element for heating the oxygen sensor to its minimum operational temperature, the oxygen sensor being received within the exhaust stream of the vehicle;

an analyzer having a user interface;

a communications link between the analyzer and a vehicle to obtain data from the oxygen sensor, the data from the oxygen sensor including a voltage, the voltage varying between an upper voltage and a lower voltage in a generally sinusoidal manner over a time period; and a diagnostic heuristic for analyzing the data and confirming proper operation of the oxygen sensor, the diagnostic heuristic being configured to combine the voltage with an elapsed time period to analyze operation of the heating element;

the diagnostic heuristic being adapted to generate an output and transmit the output to the user interface, the output including the results generated by analysis of the data by the diagnostic heuristic.

10. The diagnostic testing system of claim 9 wherein the oxygen sensor is adapted to be held below is minimum operational temperature for a predetermined period of time prior to commencing the diagnostic heuristic.

11. The diagnostic testing system of claim 9 wherein the oxygen sensor, when heated to its minimum operational temperature, includes a bias voltage.

12. The diagnostic testing system of claim 9 wherein the diagnostic heuristic includes a set of instructions presented through the user interface.

13. The diagnostic testing system of claim 9 wherein the diagnostic heuristic is configured to collect the data over a predetermined period of time for use by the diagnostic heuristic to analyze operation of the heating element.

* * * * *